United States Patent
Gnanou et al.

(10) Patent No.: US 7,709,687 B2
(45) Date of Patent: May 4, 2010

(54) DICARBANIONIC INITIATOR, A PROCESS FOR THE PREPARATION AND USE THEREOF

(75) Inventors: Yves Gnanou, Pessac (FR); Rachid Matmour, Pessac (FR); Arvind Sudhakar More, Pune (IN); Prakash Purushottam Wadgaonkar, Pune (IN)

(73) Assignee: Council Of Scientific & Industrial Research, New Delhi (IN)

( * ) Notice: Subject to any disclaimer, the term of this patent is extended or adjusted under 35 U.S.C. 154(b) by 416 days.

(21) Appl. No.: 11/539,222

(22) Filed: Oct. 6, 2006

(65) Prior Publication Data

US 2007/0197723 A1 Aug. 23, 2007

(30) Foreign Application Priority Data

Feb. 21, 2006 (IN) .................. 0479/DEL/2006

(51) Int. Cl.
  C07C 43/205 (2006.01)
  C07F 1/02 (2006.01)
  C08F 297/04 (2006.01)
  C07C 41/09 (2006.01)

(52) U.S. Cl. ............... 568/635; 568/639; 525/314; 525/245; 525/250; 525/248; 526/173; 526/181; 526/209; 526/340; 526/340.2; 260/665 R

(58) Field of Classification Search ............ 568/635, 568/639; 525/314, 245, 250, 248; 526/173, 526/181, 209, 340, 340.2; 260/665 R
  See application file for complete search history.

(56) References Cited

U.S. PATENT DOCUMENTS

| | | | | |
|---|---|---|---|---|
| 4,196,154 A | * | 4/1980 | Tung et al. | 260/665 R |
| 5,633,312 A | * | 5/1997 | Kabeta et al. | 528/14 |
| 7,297,822 B2 | * | 11/2007 | Sudhakar et al. | 568/639 |
| 2007/0197723 A1 | * | 8/2007 | Gnanou et al. | 525/88 |

OTHER PUBLICATIONS

Matmour et al. Angew. Chem. Int. Ed. 2005, 44, 284-287.*
Lo et al. Macromolecules 1994, 27, 2241-2248.*
Matmour et al. Journal of the American Chemical Society 2006, 128, 8158-8159.*
Matmour et al. Angew. Chem. Int. Ed. 2005, 44, 284-287.*
C.J. Bredeweg et al.; Studies on Dilithium Initiators; The Biomodal Molecular Weight Distribution in Polyisoprene; Macromolecules, 1994, vol. 27, No. 8 pp. 2225-2232.
Abdelaziz El Madani et al.; Kinetics of the Polymerization of isoprene initiated by α, ω-dilithiopolyisoprene in hexane; Makromol. Chem., Rapid Commun., 11, 329-335, 1990.
G.Y.S. Lo et al.; Studies on Dulithium Initiators; Effect of Additives and Seeding; Macromolecules, 1994, vol. 27, No. 8, pp. 2233-2240.

* cited by examiner

*Primary Examiner*—Vasu Jagannathan
*Assistant Examiner*—Mark S Kaucher
(74) *Attorney, Agent, or Firm*—Sughrue Mion, PLLC

(57) ABSTRACT

The present invention provides a novel dicarbanionic initiator of formula (I).

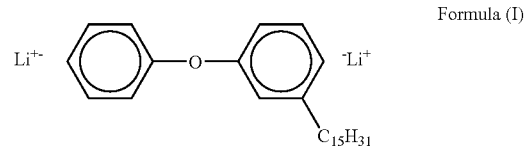

Formula (I)

The present process further provides a process for the preparation of dicarbanionic initiator of formula (I) comprising reacting 1-bromo-4-(4'-bromophenoxy)-2-pentadecyl benzene of formula (II)

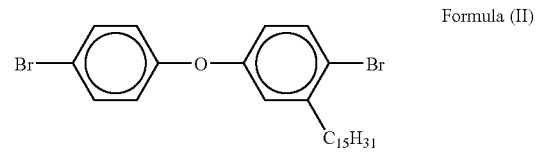

Formula (II)

with alkyllithium compound for an effecting halogen-lithium exchange reaction of 1-bromo-4-(4'-bromophenoxy)-2-pentadecyl benzene with sec-butyllithium in the presence of a non polar solvent, at a temperature in the range of 0 to 25° C. and its use as an initiator for the synthesis of telechelic polydienes and polystyrenes and SBS or SIS triblock copolymers.

15 Claims, No Drawings

DICARBANIONIC INITIATOR, A PROCESS FOR THE PREPARATION AND USE THEREOF

FIELD OF INVENTION

The present invention relates to a novel dicarbanionic initiator of formula (I) and a process for the preparation thereof. The present invention also relates to use of dicarbanionic initiator for the preparation of the α,ω-difunctional polydienes, polystyrenes and SBS or SIS triblock copolymers by anionic route in non polar solvent without using any additives.

BACKGROUND OF INVENTION

'Living' anionic polymerization is the most useful technique for the synthesis of block copolymers because of the absence of transfer and termination reactions. Among different block copolymers, ABA triblock copolymers is an important class e.g. the most well known being styrenic thermoplastic elastomers with two glassy end blocks connected to an amorphous polydiene block. One of the most versatile methods for the synthesis of such triblock copolymers is the use of a dicarbanionic initiator with a two-step sequential monomer addition sequence. However, one major difficulty met is the limited solubility of dicarbanionic initiator in non-polar solvent media that is required for the preparation of a polybutadiene or polyisoprene central block with a microstructure constituted of a high percentage of 1,4-polybutadiene or 1,4-cis-polyisoprene units, which is required for optimal elastomeric properties. The latter goal explains why a lot of patents and papers have claimed or attempted the synthesis of various carbanionic species and particularly non polar solvent-soluble organolithium initiators.

Development of an ideal difunctional organolithium initiator, usable in hydrocarbon solvents for the anionic polymerization of dienes and/or vinyl aromatic hydrocarbon monomers has been a continuing effort since the past four decades. Because of the strong association of organolithium compounds, most of the dilithium initiators require some amount of polar additives to make them soluble in hydrocarbon solvents. Adduct of 1,3-divinylbenzene with sec-BuLi was the first example of difunctional initiator studied (U.S. Pat. No. 3,862,251 (1974), C. R. Hebd. *Seances Acad. Sci.* 283, 123 (1976), *Plaste Kaustch*, 26, 263 (1979), *Makromol. Chem.*, 1985, 186, 2017). A mixture of soluble mono- and dilithiated and oligomeric species, with functionality higher than two due to possible polymerization of divinylbenzene, was obtained which did not guarantee a good control of diene polymerization. Another dianionic initiator was a bis-adduct of BuLi onto m-diisopropenylbenzene, which was an efficient bifunctional initiator in apolar solvent having good control over the molar mass and narrow molar mass distribution even in the presence of mixture of multiadduct, diadduct and unreacted sec-BuLi (*Makromol. Chem.*, 1978, 179, 551; *Polymer*, 1982, 23, 1953). To avoid precipitation of the initiator was added σ-complexing polar agent such as triethyl amine (*Macromolecules*, 1977, 10, 287; *Polymer*, 1979, 20, 1129). However, even in the presence of triethyl amine, a mixture of species was still observed after the reaction between m-diisopropenylbenzene and sec-BuLi. Some other σ-complexing polar agents such as diethyl ether, tert-butyl methyl ether, N,N,N',N'-tetramethylethylenediamine (TMEDA) and THF were found to be efficient polar additives, but leading to a high 1,2-microstructure of the polybutadiene block (*Macromolecules*, 1997, 30, 4254). It was observed that combination of the initiator seeding technique and weakly polar additives such as tert-BuOLi and anisole was necessary to prevent the presence of residual initiator and achieve equal reactivity of both end active centers so as to obtain SBS triblock copolymers with high content of 1,4-polybutadiene units (*Macromolecules*, 1997, 30, 4254; *Macromolecules*, 1997, 30, 7356). π-Complexing agents such as 1,2,4,5-tetramethylbenzene (durene) or tetraphenylethylene (TPhE) were also proposed which do not interact so strongly as σ-complexing agents with Li$^+$ cation to bring about the dissociation of the organolithium aggregates (*Polymer*, 2003, 44, 4109; *Polymer*, 2003, 44, 6205, *Polymer*, 2005, 46, 303). Other researchers concentrated their efforts on the reaction of double diphenylethylene-type molecules with a stoichiometric amount of sec-BuLi in non-polar solvents (*Polym. Prepr.*, 1984, 25 (2) 85). It was demonstrated that this difunctional initiator was efficient in the case of butadiene polymerization, but only at low monomer conversion. Dilithium initiator based on 1,3-di(1-phenylethenyl)benzene (PEB), although soluble in hydrocarbon solvents, led to bimodal molar mass distribution for molar mass lower than 50,000 and 150,000 g.mol$^{-1}$ in the cases of polystyrene and polybutadiene, respectively (*Polym. Int.*, 1991, 24, 197). Dilithium initiators based on different derivatives of double diphenylethylene-type molecules have been developed that are soluble in non-polar solvents. Although the addition reactions of these derivatives with sec-BuLi were found to be clean and rapid, the resulting dilithium initiators were insoluble forming fine suspensions, which would coagulate into hard particles after several hours (*Macromolecules*, 1994, 27, 2225; *Macromolecules*, 1994, 27, 1680; *Macromolecules*, 1994, 27, 2219). Finally, more complicated precursors such as α,ω-bis(phenylvinylidenyl)alkanes, 1,2-bis(isopropenyl-4-phenyl)ethane or (1,1,4,4-tetraphenyl)butane were developed and were found to be effective for the polymerization of dienes, but are difficult to synthesise (*Polymer*, 1981, 22, 1724; *Polymer*, 1982, 23, 73; *Polymer*, 1987, 28, 2093; *Makromol. Chem.*, 1983, 184, 1983).

Whenever high contents of 1,4-polybutadiene or 1,4-cis-polyisoprene units are desired, the anionic polymerization of dienes has to be conducted in non polar solvent media, and with lithium as the counter-ion. sec-Butyllithium has proved to be an excellent monofunctional initiator. However, until now, no bifunctional initiator exhibiting carbon-lithium bonds, and yet soluble in non polar solvent media without additives has proved really satisfactory for the synthesis of polymers such as SBS or SIS thermoplastic elastomers and α,ω-difunctional polydienes with high 1,4-polydiene microstructure. Therefore, it is of great interest and importance to synthesise new bifunctional organolithium initiator soluble in non polar solvents and its use as an initiator for the synthesis of telechelic polydienes and polystyrenes and SBS or SIS triblock copolymers by anionic route with a high content of 1,4-units in polydienes without additives in non polar solvent.

OBJECTIVES OF THE INVENTION

The main object of the present invention is to provide a novel dicarbanionic initiator of formula (I).

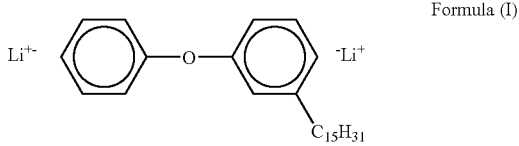

Formula (I)

Another object of the present invention is to provide a process for the preparation of dicarbanionic initiator of formula (I).

Yet another object is to provide a process for the preparation of well-defined telechelic polydienes, polystyrenes and SBS or SIS triblock copolymers with a high content of 1,4-units in polydienes in non polar solvent without additives by using bifunctional organolithium initiator of formula (I).

DETAILED DESCRIPTION OF THE INVENTION

Accordingly, the invention provides a novel dicarbanionic initiator of formula (I).

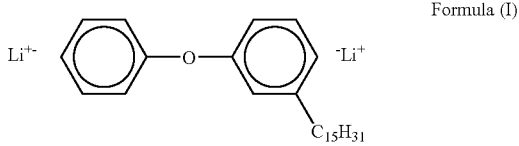

Formula (I)

The present invention further provides a process for the preparation of dicarbanionic initiator of formula (I) which comprises reacting 1-bromo-4-(4'-bromophenoxy)-2-pentadecyl benzene of formula (II)

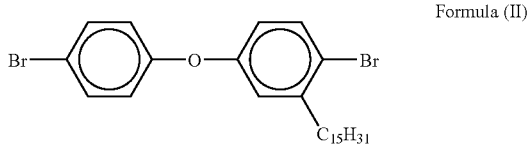

Formula (II)

with alkyllithium compound for an effecting halogen-lithium exchange reaction in the presence of a non polar solvent, at a temperature in the range of 0 to 25° C.

In an embodiment of the present invention the freeze dried 1-bromo-4-(4'-bromophenoxy)-2-pentadecyl benzene is first mixed with a non polar solvent followed by the addition of alkyllithium compound.

In yet another embodiment of the present invention the alkyllithium compound used is represented by the general formula $R_1Li$, wherein $R_1$ is a primary, secondary or tertiary alkyl, containing 2 to 20 carbon atoms per molecule.

In yet another embodiment the alkyllithium used is selected from the group consisting of ethyllithium, n-propyllithium isopropyllithium, n-butyllithium, sec-butyllithium, tert-butyllithium, pentyllithium, hexyllithium and tert-octyllithium.

In yet another embodiment the non polar solvent used is selected from the group consisting of benzene, toluene and cyclohexane.

The present invention further provides a process for the preparation of α,ω-difunctional polymer and triblock copolymer using dicarbanionic initiator of formula (I), the said process comprising the steps of:
(a) polymerizing the monomer by using dicarbanionic initiator of formula (I) in a non polar solvent, at a temperature in the range of 5 to 25° C., for a period of about 24 hours to obtain the desired α,ω-difunctional polymer in solution,
(b) capping the above said polymerization reaction by adding excess of ethylene oxide and deactivating the reaction by using degassed acidic methanol, followed by concentrating the reaction mixture and precipitating out the desired product of α,ω-difunctional polymer by using methanol; OR
(c) further, copolymerizing α,ω-difunctional polymer obtained in step (a) with styrene by adding styrene to the reaction mixture obtained in step (a) and diluting it with a mixture of non polar solvent and allowing the reaction to continue for a period of 2-6 hours, at a temperature in the range of 20 to 30° C., followed by capping, degassing, concentrating and precipitation of the desired triblock copolymer by same process as given in step (b).

In an embodiment of the present invention the α,ω-difunctional polymer obtained is selected from α,ω-difunctional polybutadienes, polyisoprenes and polystyrenes.

In yet another embodiment the triblock copolymer obtained is selected from styrene-butadiene-styrene and styrene-isoprene-styrene.

In yet another embodiment the non polar solvent used in step (a) is selected from benzene, toluene and cyclohexane.

In yet another embodiment the mixture of non polar solvent used in step (c) is a mixture of cyclohexane and tetrahydrofuran.

In yet another embodiment the concentration of tetrahydrofuran in a mixture of cyclohexane and tetrahydrofuran is about 1 vol %.

In yet another embodiment the yield of α,ω-difunctional obtained is in the range of 98 to 99%.

In still another embodiment the yield of styrene-butadiene-styrene obtained is in the range of 98 to 99%.

In still another embodiment the yield of styrene-isoprene-styrene is 97 to 98%.

Anionically polymerized polymers of conjugated dienes and/or vinyl aromatic hydrocarbons and/or other monomers can be made with dilithium initiators according to the conventional practice such as described in U.S. Pat. No. 3,734,973. Functionalized anionic polymers wherein the functionalization is terminal and/or internal are produced using dilithium initiators such as described in U.S. Pat. No. 5,393,843.

The method of synthesis of new dicarbanionic initiator and its application in the synthesis of α,ω-difunctional polybutadienes, polyisoprenes and polystyrenes and SBS or SIS triblock copolymers in non polar solvent without additives is described herein below with reference to examples, which are illustrative only and should not be construed to limit the scope of the present invention in any manner whatsoever.

EXAMPLE 1

In a flamed and vacuum dried three-necked flask, 75.0 mg ($1.39*10^{-4}$ mol) of 1-bromo-4-(4'-bromophenoxy)-2-pentadecyl benzene was freeze-dried. 3.0 mL of cyclohexane was added to make a precursor solution concentration of $5.3*10^{-2}$ mol.L$^{-1}$. 0.43 mL ($5.56*10^{-4}$ mol) of sec-butyllithium at a concentration of 1.3 M was added to the solution. After 20 minutes of reaction, 11.5 mL (7.3 g) of butadiene was added on a physical gel formed by the dicarbanionic initiator at a temperature of 5° C. The polymerization was allowed to proceed during 24 hours at room temperature and then end-capping was accomplished by addition of a large excess of ethylene oxide. The reaction was deactivated by degassed acidic methanol (3 mL of concentrated HCl in 50 mL of methanol). The reaction mixture was concentrated on a rotary evaporator. The α,ω-dihydroxyl polybutadiene was finally precipitated using methanol to give 7.1 g of a product (98%). $M_n$(SEC in THF)=51,900 g/mol; $M_w/M_n$=1.08; % 1,4-polybutadiene=90%.

EXAMPLE 2

In a flamed and vacuum dried three-necked flask, 75.0 mg ($1.39*10^{-4}$ mol) of 1-bromo-4-(4'-bromophenoxy)-2-pentadecyl benzene was freeze-dried. 3.0 mL of cyclohexane was added to make a precursor solution concentration of $5.3*10^{-2}$ mol.L$^{-1}$. 0.43 mL ($5.56*10^{-4}$ mol) of sec-butyllithium at a concentration of 1.3 M was added to the solution. After 20 minutes of reaction, 15.5 mL (9.7 g) of butadiene was added at a temperature of 5° C. The polymerization was allowed to proceed during 24 hours at room temperature. After the complete consumption of the monomer, the reaction medium was diluted with 120 mL of a mixture of cyclohexane/THF (1 vol % THF). Upon addition of 4.0 mL (3.6 g) of styrene, the colour of the medium changed instantaneously from the characteristic yellow of polybutadienyllithium carbanions to the orange colour of polystyryllithium carbanions. The polymerization was allowed to proceed during 4 hours at room temperature. The reaction was deactivated by degassed methanol. The reaction mixture was concentrated on a rotary evaporator. The SBS triblock copolymer was finally precipitated using methanol to give 13.0 g of a product (98%). $M_{n,(PB)2}$(SEC in THF)=67,400 g/mol; $M_w/M_n$=1.1. $M_{n,SBS}$(SEC in THF)= 110,900 g/mol; $M_w/M_n$=1.2. $M_n$($^1$H NMR)=93,500 g/mol; % 1,4-polybutadiene=91%.

EXAMPLE 3

In a flamed and vacuum dried three-necked flask, 75.0 mg ($1.39*10^{-4}$ mol) of 1-bromo-4-(4'-bromophenoxy)-2-pentadecyl benzene was freeze-dried. 3.0 mL of cyclohexane was added to make a precursor solution concentration of $5.3*10^{-2}$ mol.L$^{-1}$. 0.43 ml ($5.56*10^{-4}$ mol) of sec-butyllithium at a concentration of 1.3 M was added to the solution. After 20 minutes of reaction, 14.1 mL (9.6 g) of isoprene was added at room temperature. The polymerization was allowed to proceed during 8 hours at room temperature. After the complete consumption of the monomer, the reaction medium was diluted with 120 mL of a mixture of cyclohexane/THF (1 vol % THF). Upon addition of 3.5 mL (3.2 g) of styrene, the colour of the medium changed instantaneously from the characteristic yellow of polyisoprenyllithium carbanions to the orange colour of polystyryllithium carbanions. The polymerization was allowed to proceed during 4 hours at room temperature. The reaction was deactivated by degassed methanol. The reaction mixture was concentrated on a rotary evaporator. The SIS triblock copolymer was finally precipitated using methanol to give 12.4 g of a product (97%). $M_{n,(PI)2}$(SEC in THF)=69,100 g/mol; $M_w/M_n$=1.1. $M_{n,SIS}$(SEC in THF)=108,900 g/mol; $M_w/M_n$=1.2. $M_n$($^1$H NMR)=92,300 g/mol; % 1,4-polyisoprene=90%.

ADVANTAGES OF THE INVENTION

The present invention provides synthesis of new dicarbanionic initiator obtained by lithium-halogen exchange reaction of 1-bromo-4-(4'-bromophenoxy)-2-pentadecyl benzene with sec-butyllithium and its use in the synthesis of telechelic polydienes and polystyrenes and SBS or SIS triblock copolymers with high content of 1,4-polybutadiene or 1,4-cis-polyisoprene units in non polar solvent without additives.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

We claim:

1. A novel dicarbanionic initiator of formula (I):

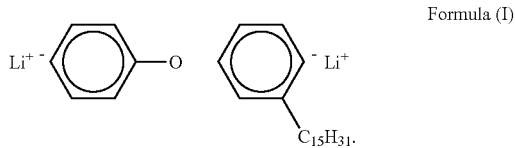

Formula (I)

2. A process for the preparation of dicarbanionic initiator of formula (I) which comprises reacting 1-bromo-4-(4'-bromophenoxy)-2-pentadecyl benzene of formula (II)

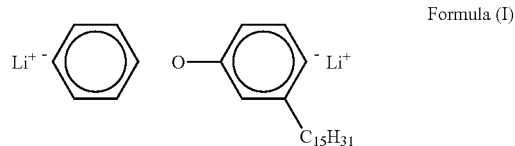

Formula (I)

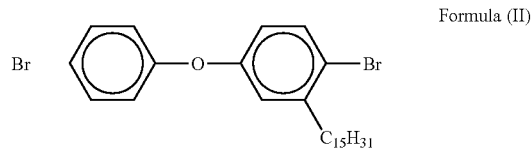

Formula (II)

with an alkyllithium compound for an effecting halogen-lithium exchange reaction in the presence of a non polar solvent, at a temperature in the range of 0 to 25° C.

3. A process as claimed in claim 2, wherein freeze dried 1-bromo-4-(4'-bromophenoxy)-2-pentadecyl benzene is first mixed with a non polar solvent followed by the addition of an alkyllithium compound.

4. A process as claimed in claim 2, wherein the alkyllithium compound used is represented by the general formula $R_1Li$, wherein $R_1$ is a primary, secondary or tertiary alkyl, containing 2 to 20 carbon atoms per molecule.

5. A process as claimed in claim 2, wherein the alkyllithium used is selected from the group consisting of ethyllithium, n-propyllithium isopropyllithium, n-butyllithium, sec-butyllithium, tert-butyllithium, pentyllithium, hexyllithium and tert-octyllithium.

6. A process as claimed in claim 2, wherein the non polar solvent used is selected from the group consisting of benzene, toluene and cyclohexane.

7. A process for the preparation of α,ω-difunctional polymer and triblock copolymer using dicarbanionic initiator of formula (I),

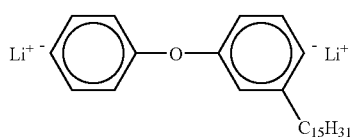

Formula (I)

said process comprising the steps of:
(a) polymerizing the monomer by using dicarbanionic initiator of formula (I) in a non polar solvent, at a temperature in the range of 5 to 25° C., for a period of about 24 hours to obtain the desired α,ω-difunctional polymer in solution, and either
(b) capping the above said polymerization reaction by adding excess of ethylene oxide and deactivating the reaction by using degassed acidic methanol, followed by concentrating the reaction mixture and precipitating out the desired product of α,ω-difunctional polymer by using methanol; or
(c) further, copolymerizing α,ω-difunctional polymer obtained in step (a) with styrene by adding styrene to the reaction mixture obtained in step (a) and diluting it with a mixture of non polar solvent and allowing the reaction to continue for a period of 2-6 hours, at a temperature in the range of 20 to 30° C., followed by capping, degassing, concentrating and precipitation of the desired triblock copolymer by same process as given in step (b).

8. A process as claimed in claim 7, wherein the non polar solvent used in step (a) is selected from the group consisting of benzene, toluene and cyclohexane.

9. A process as claimed in claim 7, wherein the mixture of non polar solvent used in step(c) is a mixture of cyclohexane and tetrahydrofuran.

10. A process as claimed in claim 9, wherein the concentration of tetrahydrofuran in a mixture of cyclohexane and tetrahydrofuran is about 1 vol %.

11. A process as claimed in claim 7, wherein the α,ω-difunctional polymer obtained is selected from α,ω-difunctional polybutadienes, polyisoprenes end polystyrenes.

12. A process as claimed in claim 7, wherein the triblock copolymer obtained is selected from styrene-butadiene-styrene and styrene-isoprene-styrene.

13. A process as claimed in claim 7, wherein the yield of α,ω-difunctional obtained is in the range of 98 to 99%.

14. A process as claimed in claim 7, wherein the triblock copolymer, obtained is styrene-butadiene-styrene, and the yield of styrene-butadiene-styrene obtained is in the range of 98 to 99%.

15. A process as claimed in claim 7, wherein the triblock copolymer obtained is styrene-isoprene-styrene, and the yield of styrene-isoprene-styrene is 97 to 98%.